United States Patent
Gouda et al.

(10) Patent No.: US 10,309,900 B1
(45) Date of Patent: *Jun. 4, 2019

(54) BIOLOGICAL SUBSTANCE QUANTITATION METHOD, PATHOLOGICAL DIAGNOSIS SUPPORT SYSTEM AND RECORDING MEDIUM STORING COMPUTER READABLE PROGRAM

(71) Applicant: Konica Minolta, Inc., Tokyo (JP)

(72) Inventors: Hideki Gouda, Tokyo (JP); Kensaku Takanashi, Hino (JP); Kohsuke Gonda, Sendai (JP); Noriaki Ohuchi, Sendai (JP); Mika Watanabe, Sendai (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/256,224

(22) Filed: Jan. 24, 2019

Related U.S. Application Data

(63) Continuation of application No. 15/549,006, filed as application No. PCT/JP2015/053679 on Feb. 10, 2015, now Pat. No. 10,234,391.

(51) Int. Cl.
| | |
|---|---|
| *H04N 7/18* | (2006.01) |
| *G06K 9/00* | (2006.01) |
| *G01N 21/64* | (2006.01) |
| *G01N 33/483* | (2006.01) |
| *G01N 33/58* | (2006.01) |
| *G06T 7/90* | (2017.01) |

(Continued)

(52) U.S. Cl.
CPC ......... *G01N 21/6428* (2013.01); *G01N 21/64* (2013.01); *G01N 21/6486* (2013.01);
(Continued)

(58) Field of Classification Search
CPC ....... G06K 9/00; G01N 21/6428; G06F 19/18
(Continued)

(56) References Cited

U.S. PATENT DOCUMENTS

| | | | | |
|---|---|---|---|---|
| 2009/0086314 A1* | 4/2009 | Namba | ............... | G01N 21/6458 359/383 |
| 2011/0249137 A1* | 10/2011 | Suzuki | ............... | G01N 21/6428 348/222.1 |

(Continued)

FOREIGN PATENT DOCUMENTS

| | | |
|---|---|---|
| EP | 2833123 A1 | 2/2015 |
| EP | 2833138 A1 | 2/2015 |

(Continued)

OTHER PUBLICATIONS

International Search Report dated May 19, 2015 for PCT/JP2015/053679 and English translation.

(Continued)

Primary Examiner — Seyed H Azarian
(74) Attorney, Agent, or Firm — Lucas & Mercanti, LLP

(57) ABSTRACT

A biological substance quantitation method includes the following. A fluorescent image is input, which represents an expression of a specific biological substance in a sample stained with a fluorescent substance by a florescent bright spot. A quantitative evaluation value of the florescent bright spot is calculated. A standard fluorescent image of a standard sample stained under a same condition as the sample and representing an expression of the biological substance in a standard sample, is input under a same condition as the fluorescent image. A quantitative evaluation value in the standard fluorescent image is calculated under a same condition as the fluorescent image. Based on a correlation between an expression amount of the biological substance in a standard sample measured in advance and the evaluation value in the standard fluorescent image, the evaluation value in the fluorescent image is converted to an expression amount of the biological substance in the sample.

9 Claims, 6 Drawing Sheets

(51) Int. Cl.
*G01N 21/93* (2006.01)
*G06T 7/00* (2017.01)
*G01N 33/53* (2006.01)
*G01N 33/48* (2006.01)
*G01N 33/50* (2006.01)

(52) U.S. Cl.
CPC ............ *G01N 21/93* (2013.01); *G01N 33/48* (2013.01); *G01N 33/483* (2013.01); *G01N 33/5023* (2013.01); *G01N 33/53* (2013.01); *G01N 33/582* (2013.01); *G06T 7/0016* (2013.01); *G06T 7/90* (2017.01); *G06T 2207/30024* (2013.01)

(58) Field of Classification Search
USPC ....... 382/100, 103, 106, 128–134, 162, 168, 382/181, 189, 203, 209, 219, 224, 232, 382/254, 274, 27, 6, 285–291, 305, 312, 382/321; 506/8; 348/79, 222.1; 359/383; 435/7.23
See application file for complete search history.

(56) References Cited

U.S. PATENT DOCUMENTS

2013/0230866 A1* 9/2013 Miyashita .......... G01N 21/6428 435/7.23
2013/0338014 A1    12/2013 McDonough
2013/0338016 A1* 12/2013 McDonough ........ G01N 33/582 506/8
2014/0267672 A1*  9/2014 Morrison .......... G01N 21/6458 348/79
2014/0314299 A1* 10/2014 Santamaria-Pang ........................ G06K 9/0014 382/133

FOREIGN PATENT DOCUMENTS

| JP | 2013057631 A  | 3/2013  |
| WO | 2013/033060 A1 | 3/2013  |
| WO | 2013146694 A1 | 10/2013 |
| WO | 2013146843 A1 | 10/2013 |
| WO | 2015002082 A1 | 1/2015  |

OTHER PUBLICATIONS

Written Opinion of the International Searching Authority dated May 19, 2015 from corresponding International Application No. PCT/JP2015/053679 and English translation.
Extended European Search Report dated Dec. 8, 2017 from the corresponding European Application No. 15881936.7.
Office Action dated Oct. 8, 2018 from the corresponding European Application No. 15881936.7.
Notification of Refusal dated Aug. 7, 2018 from the corresponding Japanese Application No. JP 2016-574558 and English translation.

* cited by examiner

BIOLOGICAL SUBSTANCE QUANTITATION METHOD, PATHOLOGICAL DIAGNOSIS SUPPORT SYSTEM AND RECORDING MEDIUM STORING COMPUTER READABLE PROGRAM

CROSS REFERENCE TO RELATED APPLICATIONS

This application is a continuation application of U.S. application Ser. No. 15/549,006, filed Aug. 4, 2017, which was a 371 of PCT/JP2015/053679, filed Feb. 10, 2015, the priority of both applications is claimed, and both applications are incorporated herein by reference.

TECHNOLOGICAL FIELD

The present invention relates to a method for quantitating a biological substance, a pathological diagnosis support system, and a program using luminance information of a fluorescent substance.

BACKGROUND ART

In recent years, with the spread of therapy using molecular target drugs based mainly on antibody drugs, quantitating a biological substance in cells of the observation target has been desired for more efficient design of the molecular target drugs. For confirming the presence of a specific biological substance, a method of tissue analysis is known on the basis of staining of cells using a fluorescent substance specifically bindable to the biological substance.

Patent Document 1 proposes a method of improving accuracy in quantitating the expression amount of biological substance by measuring the number of fluorescent bright spot in the tissue sample as follows: staining the tissue sample with a phosphor bindable to the biological substance, analyzing peaks in the luminance distribution of the fluorescent bright spot in the tissue sample, and calculating average luminance of one particle of the phosphor.

PRIOR ART DOCUMENT

Patent Document

Patent Document 1: Japanese Patent Application Laid-Open Publication No. 2013-57631

SUMMARY

Problems to be Solved by the Invention

However, it is generally known that errors often occur in quantitation result of a biological substance from a stained tissue sample due to, for example, variations in staining conditions (for example, reaction time, concentration of solvent, and temperature), different operator, or different measurement system (for example, measuring instrument such as microscope and camera).

According to the conventional technique described in patent document 1, there is a problem that the analysis result often varies due to different operator or different measurement system in performing comparison analysis of quantitation results of a biological substance obtained from a plurality of samples.

In a pathological diagnosis, it is desired that evaluation by comparing quantitation results is possible not only between samples from which biological substance quantitation is performed at the same time but also between samples obtained by different operator, different measurement instrument, or different staining conditions, i.e., the diagnosis result of one patient is desired to be compared before after conducting treatment.

A main object of the present invention is to provide a biological substance quantitation method and a program for accurate quantitation of a specific biological substance in a sample by correcting errors caused by the difference in operator and measurement system.

Means for Solving the Problem

To achieve at least one of the abovementioned objects, according to an aspect of the present invention, there is provided a biological substance quantitation method which quantitates an expression amount of a specific biological substance in a sample stained with a staining reagent which stains the biological substance with a fluorescent substance, the method including:

inputting a fluorescent image which represents an expression of the biological substance in the sample by a fluorescent bright spot;

performing fluorescence quantitation which includes calculation of an evaluation value by quantitative evaluation of the fluorescent bright spot in the fluorescent image;

inputting a standard fluorescent image under a same condition as the inputting of the fluorescent image, wherein
the standard fluorescent image represents an expression of the biological substance in a standard sample by a fluorescent bright spot based on staining under a same condition as the sample, and
an expression amount of the biological substance in the standard sample is measured in advance;

performing standard fluorescence quantitation which includes calculation of an evaluation value by quantitative evaluation of the fluorescent bright spot in the standard fluorescent image under a same condition as the quantitation of fluorescence;

calculating a correlation between the expression amount of the biological substance in the standard sample and the evaluation value of the fluorescent bright spot in the standard fluorescent image; and converting the evaluation value of the fluorescent bright spot in the fluorescent image to an expression amount of the biological substance in the sample based on the calculating of the correlation.

To achieve at least one of the abovementioned objects, according to another aspect of the present invention, there is provided a pathological diagnosis support system which quantitates an expression amount of a specific biological substance in a sample stained with a staining reagent which stains the biological substance with a fluorescent substance, the system including:

a fluorescent image inputting unit which inputs a fluorescent image which represents an expression of the biological substance in the sample by a fluorescent bright spot;

a fluorescence quantitation unit which calculates an evaluation value by quantitative evaluation of the fluorescent bright spot in the fluorescent image;

a standard fluorescent image inputting unit which inputs a standard fluorescent image under a same condition as the fluorescent image inputting unit, wherein
the standard fluorescent image represents an expression of the biological substance in a standard sample by a fluorescent bright spot based on staining under a same condition as the sample, and an expression amount of the biological substance in the standard sample is measured in advance;

a standard fluorescent quantitation unit which calculates an evaluation value by quantitative evaluation of the fluorescent bright spot in the standard fluorescent image under a same condition as the fluorescence quantitation unit;

a correlation calculator which calculates a correlation between the expression amount of the biological substance in the standard sample and the evaluation value of the fluorescent bright spot in the standard fluorescent image; and a converter which converts the evaluation value of the fluorescent bright spot in the fluorescent image to an expression amount of the biological substance in the sample based on the correlation.

To achieve at least one of the above-mentioned objects, according to another aspect of the present invention, there is provided a program causing a computer which quantitates an expression amount of a specific biological substance in a sample stained with a staining reagent which stains the biological substance with fluorescent substances, to function as:

a fluorescent image inputting unit which inputs a fluorescent image which represents an expression of the biological substance in the sample by a fluorescent bright spot;

a fluorescence quantitation unit which calculates an evaluation value by quantitative evaluation of the fluorescent bright spot in the fluorescent image;

a standard fluorescent image inputting unit which inputs a standard fluorescent image under a same condition as in the fluorescent image inputting unit, wherein the standard fluorescent image represents an expression of the biological substance in a standard sample by a fluorescent bright spot based on staining under a same condition as the sample, and an expression amount of the biological substance in the standard sample is measured in advance;

a standard fluorescent quantitation unit which calculates an evaluation value by quantitative evaluation of the fluorescent bright spot in the standard fluorescent image under a same condition as the fluorescence quantitation unit;

a correlation calculator which calculates a correlation between the expression amount of the biological substance in the standard sample and the evaluation value of the fluorescent bright spot in the standard fluorescent image; and a converter which converts the evaluation value of the fluorescent bright spot in the fluorescent image to an expression amount of the biological substance in the sample based on the correlation.

Advantageous Effects of Invention

According to the present invention, the amount of a specific biological substance in a sample can be accurately quantitated.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

EMBODIMENT FOR CARRYING OUT THE INVENTION

Embodiments for carrying out the present invention will now be described with reference to the attached drawings, which should not be construed to limit the present invention.

Configuration of Pathological Diagnosis Support System 100

Figure 1:
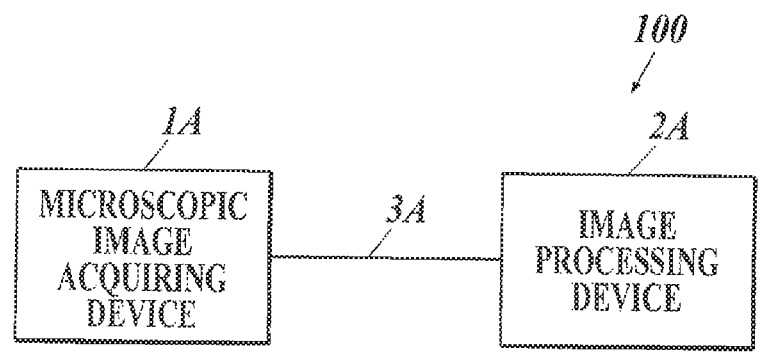
FIG. 1 is a diagram showing a configuration of a pathological diagnosis assistance system using the biological substance quantitation method according to the present invention.

FIG. 1 illustrates an exemplary overall configuration of a pathological diagnosis support system 100 that employs the quantitative determination method of a biological substance according to the present invention. The pathological diagnosis support system 100 acquires microscopic images of a sample of observation target (hereinafter referred to as a "target sample") and a sample in which concentration of a specific biological substance is quantitated in advance (hereinafter referred to as a "standard sample"), analyzes the acquired microscopic images, and outputs a feature quantity which quantitatively represents expression of the specific biological substance in the target sample of observation target.

As illustrated in FIG. 1, the pathological diagnosis support system 100 includes a microscopic image acquiring device 1A, an image processing device 2A, and an interface, such as a cable 3A, connecting the microscopic image acquiring device 1A and the image processing device 2A for transmission and reception of data. The microscopic image acquiring device 1A may be connected to the image processing device 2A in any manner. For example, the microscopic image acquiring device 1A and the image processing device 2A may be connected through a local area network (LAN) or wireless communication.

The microscopic image acquiring device 1A is a known optical microscope provided with a camera, which acquires a microscopic image of a tissue sample on a microscopic slide placed on a slide fixation stage, and transmits the microscopic image to the image processing device 2A.

The microscopic image acquiring device 1A includes an irradiator, a focusing unit, a photographing unit, and a communication interface (I/F). The irradiator includes a light source and a filter, and emits light toward the tissue sample on the microscopic slide placed on the slide fixation stage. The focusing unit includes an eyepiece lens and an object lens. The focusing unit focuses transmitted light, reflected light, or fluorescent light, which is emitted from the tissue sample on the microscopic slide in response to the irradiated light, into an image. The photographing unit includes a charge coupled device (CCD) sensor. The photographing unit is specifically a camera disposed in a microscope to photograph an image formed by the focusing unit, and produce the digital image data of the microscopic image. The communication interface transmits the image data of the microscopic image to the image processing device 2A. The microscopic image acquiring device 1A in the present embodiment includes a bright field unit suitable for bright field microscopy composed of a combination of an irradiating subunit and a focusing subunit, and a fluorescence unit suitable for fluorescent microscopy composed of a combination of an irradiating subunit and a focusing subunit, and can switch between these units, i.e., between bright field observation and fluorescence observation.

Besides the microscope provided with a camera, the microscopic image acquiring device 1A may be any device, for example, a virtual microscopic slide preparing device that scans a microscopic slide placed on a slide fixation stage of a microscope to acquire a microscopic image of an overall tissue sample (see Japanese Publication of International Patent Application No. 2002-514319, for example). The virtual microscopic slide preparing device can acquire image data of the overall tissue sample that can be displayed on a display at once.

The image processing device 2A analyzes the microscopic image transmitted from the microscopic image acquiring device 1A to calculate the distribution of the expression of the specific biological substance in the target tissue sample.

Figure 2:
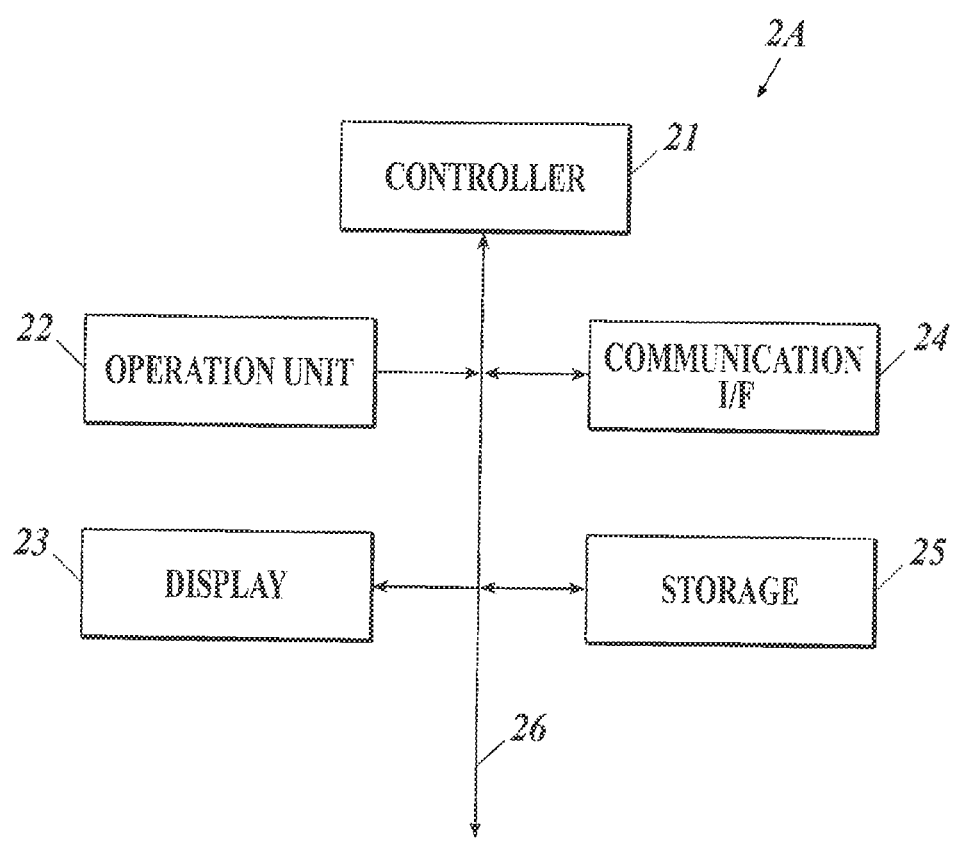
FIG. 2 is a block diagram showing a functional configuration of an image processing device in FIG. 1.

FIG. 2 illustrates an exemplary functional configuration of the image processing device 2A. As illustrated in FIG. 2, the image processing device 2A includes a controller 21, an operating unit 22, a display 23, a communication interface 24, and a storage 25, which are connected to each other through a bus 26.

The controller 21 includes a central processing unit (CPU), a random access memory (RAM), and the like. The controller 21 executes multiple processes in cooperation with a variety of programs stored in the storage 25 to control the overall operation of the image processing device 2A. For example, the controller 21 executes image analysis in cooperation with a program stored in the storage 25 (see steps S4 to S6 in FIG. 5) to and functions as a unit executing a fluorescent quantitation step, standard fluorescence quantitation step, correlation calculation step, and conversion step.

The operating unit 22 includes a keyboard including keys for inputting characters and numbers and several functional keys, and a pointing device, such as a mouse. The operating unit 22 outputs input signals to the controller 21, i.e., signals generated by press of keys on the keyboard and by operation of the mouse.

The display 23 includes a monitor, such as a cathode ray tube (CRT) display or a liquid crystal display (LCD). The display 23 displays a variety of windows in response to display signals input from the controller 21.

The communication interface 24 allows data transmission and reception between the microscopic image acquiring device 1A and external devices, such as the microscopic image acquiring device 1A. The communication interface 24 functions as an input unit of inputting a standard fluorescent image and a fluorescent image.

The storage 25 includes a hard disk drive (HDD) or a nonvolatile memory composed of a semiconductor, for example. The storage 25 stores a variety of programs and data as described above.

Besides, the image processing device 2A may include a LAN adaptor and a router to be connected to external devices through a communication network, such as a LAN.

The image processing device 2A in the present embodiment preferably analyzes the sample using the bright field image and fluorescent image transmitted from the microscopic image acquiring device 1A.

Figure 3:
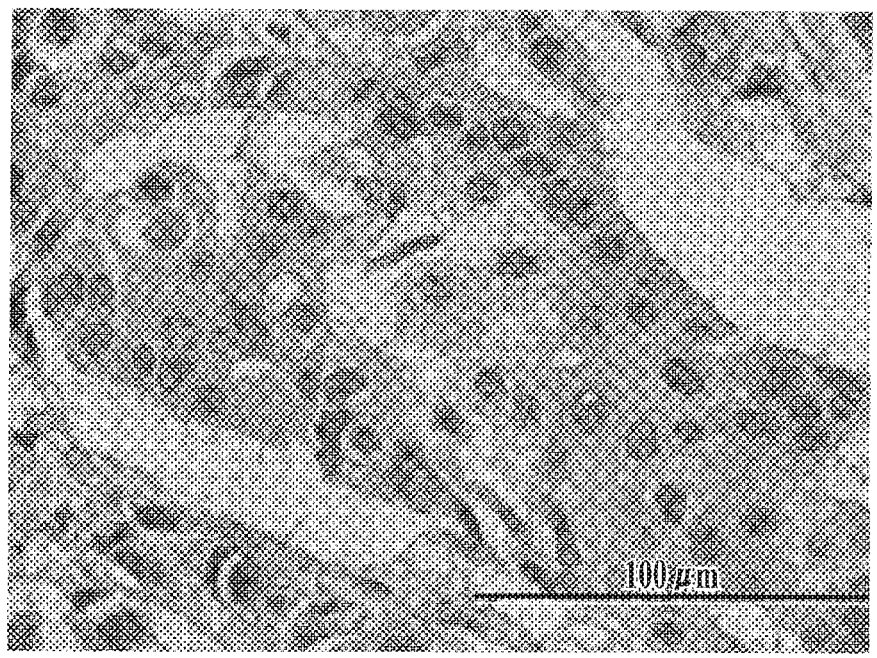
FIG. 3 is a diagram illustrating an exemplary bright field image.

The bright field image is a microscopic image of a sample stained with a hematoxylin (H) staining reagent or a hematoxylin-eosin (HE) staining reagent focused and photographed in the bright field with the microscopic image acquiring device 1A. The bright field image represents morphology of cells in the sample. The hematoxylin is a blue violet dye for staining basophilic tissues, such as cell nuclei, bone tissues, part of cartilaginous tissues, and serum components. The eosin is a red to pink color dye for staining acidophilic tissues, such as cytoplasms, connective tissues of soft tissues, erythrocytes, fibrin, and endocrine granules. FIG. 3 illustrates an exemplary bright field image of an HE-stained tissue sample.

Figure 4:
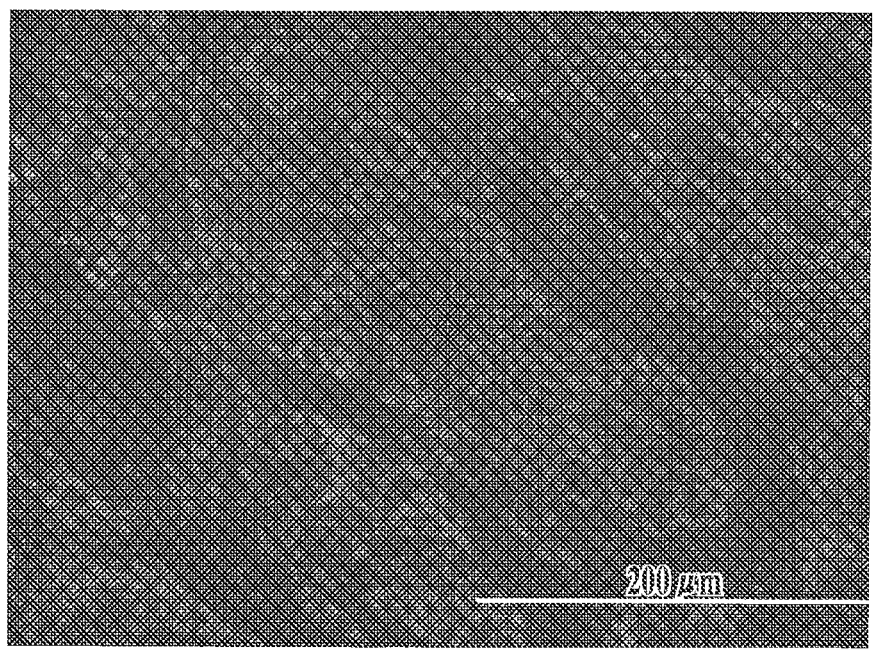
FIG. 4 is a diagram illustrating an exemplary fluorescent image.

The fluorescent image is a microscopic image obtained as follows: A sample is stained with a staining reagent containing a fluorescent substance bonded to a biological substance recognition site which specifically bonds or reacts with the specific biological substance. The sample is irradiated with an excitation light having a predetermined wavelength in the microscopic image acquiring device 1A so that the fluorescent substance emits light (fluorescent light). The fluorescent light is enlarged, focused, and photographed. In other words, the fluorescent light in the fluorescent image represents the expression of the specific biological substance corresponding to the biological substance recognition site in the sample. FIG. 4 illustrates an exemplary fluorescent image.

Acquisition of Fluorescent Image

A method of acquiring the fluorescent image will now be described in detail, including the staining reagent used in acquisition of a fluorescent image and the method of staining a sample with the staining reagent.

[Fluorescent Substance]

Examples of the fluorescent substance used as the staining reagent for acquiring a fluorescent image include an organic fluorescent dye and a quantum dot (a semiconductor particle). The fluorescent substances preferably emit a visible light to a near-infrared light having a wavelength in the range of 400 to 1100 nm when excited by an ultraviolet light to a near-infrared light having a wavelength in the range of 200 to 700 nm.

Examples of the organic fluorescent dyes include fluorescein dye molecules, rhodamine dye molecules, Alexa Fluor (registered trademark, made by Invitrogen Corporation) dye molecules, BODIPY (registered trademark, made by Invitrogen Corporation) dye molecules, cascading dye molecules, coumarin dye molecules, eosin dye molecules, NBD dye molecules, pyrene dye molecules, Texas Red dye molecules, and cyanine dye molecules.

Specific examples thereof include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7, 7'-tetrachlorofluorescein, 6-carboxy-4',5'-dichloro-2',7'-dimethoxyfluorescein, naphthofluorescein, 5-carboxyrhodamine, 6-carboxy-rhodamine, 5,6-dicarboxyrhodamine, rhodamine 6G, tetramethylrhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (made by Invitrogen Corporation), methoxycoumarin, eosin, NBD, pyrene, Cy5, Cy5.5, and Cy7. These organic fluorescent dyes may be used alone or in combination.

The quantum dot may contain Group II-VI compounds, Group III-V compounds, or Group IV elements as a component (also referred to as a "Group II-VI quantum dot", "Group III-V quantum dot", or "Group IV quantum dot", respectively) can be used. These quantum dots may be used alone or in combination.

Specific examples thereof include, but should not be limited to, CdSe, CdS, CdTe, ZnSe, ZnS, ZnTe, InP, InN, InAs, InGaP, GaP, GaAs, Si, and Ge.

[Fluorescent Substance-Encapsulating Nanoparticle]

The fluorescent substance used as a staining reagent for obtaining a fluorescent image in the present embodiment may be a fluorescent substance-encapsulating nanoparticle (hereinafter, referred to as a fluorescent particle) in which a plurality of molecules of the fluorescent substance are accumulated. The fluorescent particle refers to a nanoparticle in which the fluorescent substance is dispersed. The fluorescent substance and the nanoparticle may or may not be chemically bonded with each other. The material composing the nanoparticle is not particularly limited, and examples thereof include silica, polystyrene, polyactate acid, melamine, and the like.

A quantum dot having a core of a quantum dot and an outer shell may be used as a fluorescent particle. Throughout the specification, the quantum dot having a shell is represented, for example, as CdSe/ZnS where the core is CdSe and the shell is ZnS. Examples of usable quantum dots having a core of a quantum dot and a shell include, but should not be limited to, CdSe/ZnS, CdS/ZnS, InP/ZnS, InGaP/ZnS, Si/SiO$_2$, Si/ZnS, Ge/GeO$_2$, Ge/ZnS.

A quantum dot having a surface treated with an organic polymer may also be used when necessary. Examples of such quantum dots include CdSe/ZnS having surface carboxy groups (made by Invitrogen Corporation), and CdSe/ZnS having surface amino groups (made by Invitrogen Corporation).

The fluorescent particle used in the present embodiment can be prepared by any known method. Encapsulation of a fluorescent dye in the nanoparticle may be performed by any method, for example, particle synthesis by bonding a fluorescent dye molecule to a raw-material monomer, or introduction of a fluorescent dye by adsorbing into the resin.

For example, a polystyrene nanoparticle encapsulating an organic fluorescent dye can be prepared by a copolymerization process using an organic dye having a polymerizable functional group as described in U.S. Pat. No. 4,326,008 (1982), or by impregnation of a polystyrene nanoparticle with an organic fluorescent dye as described in U.S. Pat. No. 5,326,692 (1992).

A polymer nanoparticle encapsulating quantum dots can be prepared by impregnation of a polystyrene nanoparticle with quantum dot, which is disclosed in Nature Biotechnology vol. 19, p. 631 (2001).

The fluorescent particle used in the present embodiment may have any average particle size, but is preferably 40 to 280 nm. Too large average particle size readily results in saturation of luminance and inaccurate measurement when fluorescent particles are close to each other. When the average particle size is small, integrated value of luminance of one fluorescent particle is small and the fluorescent signal is easily buried in background noises (noises of camera or autofluorescence of cells).

The average particle size is determined as follows: Cross-sectional area of each particle is measured in an electron microscopic photograph taken with a scanning electron microscope (SEM). The observed area of each particle is regarded as the area of a circle, and the diameter of the circle is determined as the particle size. In the present application, the sizes of 1000 particles are measured, and the arithmetic average of them is determined as the average particle size.

[Binding of Biological Substance Recognition Site to Fluorescent Particle]

The biological substance recognition site according to the present embodiment is a site specifically bindable and/or reactive to a target biological substance. The target biological substance may be any biological substance specifically bindable to the site. Typical examples of the target biological substance include proteins (peptides), nucleic acids (oligonucleotides, polynucleotides), and antibodies. Accordingly, examples of a substance specifically bindable to the target biological substance include antibodies that can recognize the proteins as antigens, other proteins specifically bindable to the proteins, and nucleus acids having base sequences allowing hybridization to the nucleus acids. Specific examples thereof include an anti-HER2 antibody specifically bindable to HER2 or a protein to be expressed on surfaces of cells; a Ki67 antibody specifically bindable to Ki67 protein as a cell proliferation marker to be expressed in cell nuclei; an anti-ER antibody specifically bindable to an estrogen receptor (ER) to be expressed in cell nuclei; and an anti-actin antibody specifically bindable to actin that forms a cell skeleton. Among these antibodies, the anti-HER2 antibody, the anti-ER antibody, or the anti-Ki67 antibody is preferred because a fluorescent particle bonded to them can be used in selection of drugs for breast cancer.

Examples of the specific antigens include the followings. The antibodies for recognizing these antigens are commercially available from a variety of antibody manufacturers, and can also be produced based on knowledge generally shared. Examples of the specific antigens include M. actin, M.S. actin, S.M. actin, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, c-KIT, c-MET, collagen type IV, Cox-2, cyclin D1, keratin, cytokeratin (high molecular weight), pan-keratin, pan-keratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, factor VIII-related antigen, fascin, FSH, galectin-3, gastrin, GFAP, glucagon, glycophorin A, granzyme B, hCG, hGH, *Helicobacter pylori*, HBc antigen, HBs antigen, hepatocyte specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kip1), p53, p53, P63, PAX 5, PLAP, *Pneumocystis carinii*, Podoplanin (D2-40), PGR, prolactin, PSA, prostatic acid phosphatase, renal cell carcinoma, S100, somatostatin, spectrin, synaptophysin, TAG-72, TdT, thyroglobulin, TSH, TTF-1, TRAcP, tryptase, bilin, vimentin, WT1, and Zap-70.

In the case where the target biological substance is a nucleus acid, the following specific nucleus acid genes whose relations with diseases are pointed out can be exemplified. Probes recognizing these specific nucleus acid genes are commercially available as BAC probes, and can also be produced based on knowledge generally shared. Specific examples of the specific nucleus acid genes are listed below. Examples of genes related to proliferation of cancer or response rates of molecular target drugs include HER2, TOP2A, HER3, EGFR, P53, and MET. Known examples of cancer related genes are as follows. Examples of tyrosine kinase related genes include ALK, FLT3, AXL, FLT4 (VEGFR3, DDR1, FMS(CSF1R), DDR2, EGFR(ERBB1), HER4(ERBB4), EML4-ALK, IGF1 R, EPHA1, INSR, EPHA2, IRR(INSRR), EPHA3, KIT, EPHA4, LTK, EPHA5, MER(MERTK), EPHA6, MET, EPHA7, MUSK, EPHA8, NPM1-ALK, EPHB1, PDGFRα(PDGFRA), EPHB2, PDGFRβ(PDGFRB)EPHB3, RET, EPHB4, RON (MST1R), FGFR1, ROS(ROS1), FGFR2, TIE2(TEK), FGFR3, TRKA(NTRK1), FGFR4, TRKB(NTRK2), FLT1 (VEGFR1), and TRKC(NTRK3). Examples of breast cancer related genes include ATM, BRCA1, BRCA2, BRCA3, CCND1, E-Cadherin, ERBB2, ETV6, FGFR1, HRAS, KRAS, NRAS, NTRK3, p53, and PTEN. Examples of genes related to carcinoid tumors include BCL2, BRD4, CCND1, CDKN1A, CDKN2A, CTNNB1, HES1, MAP2, MEN1, NF1, NOTCH1, NUT, RAF, SDHD, and VEGFA. Examples of colorectal cancer related genes include APC, MSH6, AXIN2, MYH, BMPR1A, p53, DCC, PMS2, KRAS2 (or Ki-ras), PTEN, MLH1, SMAD4, MSH2, STK11, and MSH6. Examples of lung cancer related genes include ALK, PTEN, CCND1, RASSF1A, CDKN2A, RB1, EGFR, RET, EML4, ROS1, KRAS2, TP53, and MYC. Examples of liver cancer related genes include Axinl, MALAT1, b-catenin, p16 INK4A, c-ERBB-2, p53, CTNNB1, RB1, Cyclin D1, SMAD2, EGFR, SMAD4, IGFR2, TCF1, and KRAS. Examples of kidney cancer related genes include Alpha, PRCC, ASPSCR1, PSF, CLTC, TFE3, p54nrb/NONO, and TFEB. Examples of thyroid cancer related genes include AKAP10, NTRK1, AKAP9, RET, BRAF, TFG, ELE1, TPM3, H4/D10S170, and TPR. Examples of ovarian cancer related genes include AKT2, MDM2, BCL2, MYC, BRCA1, NCOA4, CDKN2A, p53, ERBB2, PIK3CA, GATA4, RB, HRAS, RET, KRAS, and RNASET2. Examples of prostate cancer related genes include AR, KLK3, BRCA2, MYC, CDKN1B, NKX3.1, EZH2, p53, GSTP1, and PTEN. Examples of bone tumor related genes include CDH11, COL12A1, CNBP, OMD, COL1A1, THRAP3, COL4A5, and USP6.

The biological substance recognition site may be bonded to a fluorescent particle with any bond. Examples of the bonding form include covalent bond, ionic bond, hydrogen bond, coordination bond, physical adsorption, and chemical adsorption. Bonds having strong forces, such as covalent bond, are preferred in view of stability of the bond.

An organic molecule may link between the biological substance recognition site and the fluorescent particle. For example, a poly(ethylene glycol) chain, such as SM(PEG)12 made by Thermo Scientific Inc., may be used to inhibit non-specific adsorption of a biological substance.

For example, the biological substance recognition site is bonded to fluorescent substance-encapsulating a silica nanoparticle according to the same procedure in both the fluorescent substance composed of an organic fluorescent dye and that composed of a quantum dot. For example, the biological substance recognition site may be bonded to a fluorescent substance-encapsulating silica nanoparticle with a silane coupling agent, which is widely used in bonding an inorganic substance to an organic substance. The silane coupling agent has an alkoxysilyl group at one terminal of the molecule to yield a silanol group through hydrolysis, and has a functional group, such as a carboxyl, amino, epoxy, or aldehyde group, at the other terminal. The silane coupling agent binds to an inorganic substance through an oxygen atom of the silanol group. Specific examples thereof include mercaptopropyltriethoxysilane, glycidoxypropyltriethoxysilane, aminopropyltriethoxysilane, and silane coupling agents having a poly(ethylene glycol) chain (such as PEG-silane no. SIM6492.7 made by Gelest, Inc.). Two or more silane coupling agents may be used in combination.

The organic fluorescent dye-encapsulating nanoparticle may be reacted with a silane coupling agent according to a known procedure. For example, the organic fluorescent dye-encapsulating nanoparticle is dispersed in pure water, and aminopropyltriethoxysilane is added to be reacted with the particle at room temperature for 12 hours. After the reaction is completed, the product is centrifuged or filtered to yield organic fluorescent dye-encapsulating nanoparticle having a surface modified with an aminopropyl group. The amino group can be reacted with a carboxyl group in an antibody, so that the antibody is bonded to the organic fluorescent dye-encapsulating nanoparticle through an amido bond. A condensing agent, such as EDC (1-ethyl-3-[3-dimethylaminopropyl]carbodiimide hydrochloride: available from Pierce (registered trademark)), may also be used when necessary.

A linker compound having a site that can be directly bonded to an organic fluorescent dye-encapsulating nanoparticle modified with an organic molecule and a site that can be bonded to a molecular target substance may be used when necessary. Specifically, in use of sulfo-SMCC (sulfo-succinimidyl 4[N-maleimidomethyl]-cyclohexane-1-carboxylate: available from Pierce) having both a site selectively reactive with an amino group and a site selectively reactive with a mercapto group, the amino group of the organic fluorescent dye-encapsulating nanoparticle modified with aminopropyltriethoxysilane can be bonded to a mercapto group in the antibody, so that an organic fluorescent dye-encapsulating nanoparticle bonded with an antibody is formed.

When the biological substance recognition site is bonded to each fluorescent substance-encapsulating polystyrene nanoparticle, the same procedure can be used both in the case where the fluorescent substance is an organic fluorescent dye and in the case where the fluorescent substance is a quantum dot. In other words, impregnation of a polystyrene nanoparticle having a functional group, such as an amino group, with an organic fluorescent dye or a quantum dot can yield a fluorescent substance-encapsulating polystyrene nanoparticle having the functional group. Use of EDC or sulfo-SMCC in the subsequent step can yield a fluorescent substance-encapsulating polystyrene nanoparticle having an antibody.

[Staining Process]

The method of staining a tissue sample will now be described. Samples prepared by any known method can be applied to the staining process described below.

The quantitation method according to the present invention can be applied not only to a paraffin-embedded tissue sample but also to a cell sample fixed onto a substrate and the like.

1) Deparaffinizing Step

A tissue sample is immersed in xylene in a vessel to remove paraffin at any temperature, for example, at room temperature. A preferred immersion time is 3 minutes or more and 30 minutes or less. Xylene may be replaced with fresh one during the immersion as needed.

The tissue sample is then immersed in ethanol in a vessel to remove xylene. The immersion may be performed at any temperature, for example, at room temperature. A preferred immersion time is 3 minutes or more and 30 minutes or less. Ethanol may be replaced with fresh one during the immersion as needed.

The tissue sample is then immersed in water in a vessel to remove ethanol at any temperature, for example, at room temperature. A preferred immersion time is 3 minutes or more and 30 minutes or less. Water may be replaced with fresh one during the immersion as needed.

2) Retrieval Process

A target biological substance is retrieved by a known process. The retrieval may be performed under any condition, and a solution for retrieval may be, for example, a 0.01M citric acid buffer solution (pH: 6.0), a 1 mM EDTA solution (pH: 8.0), 5% urea, or a 0.1M trishydrochloric acid buffer solution. An autoclave, a microwave, a pressure pan, or a water bath may be used as a heater. The retrieval may be performed at any temperature, for example, at room temperature. The sample may be retrieved at a temperature of 50 to 130° C. for 5 to 30 minutes.

The activated sample is then immersed in phosphate buffered saline (PBS) in a vessel to wash the sample at any temperature, for example, at room temperature. A preferred immersion time is 3 minutes or more and 30 minutes or less. PBS may be replaced with fresh one during the immersion as needed.

3) Staining with Fluorescent Particle Bonded to Biological Substance Recognition Site A dispersion of the fluorescent particle bonded to a biological substance recognition site in PBS is placed on a tissue sample to react with a target biological substance. The type of the biological substance recognition site bindable to the fluorescent particle can be varied to stain a variety of biological substances. In use of several types of fluorescent particle bonded to different biological substance recognition sites, these types of fluorescent particle bonded to different biological substance recognition sites in PBS may be premixed, or may be sequentially placed on the tissue sample.

The staining may be performed at any temperature, for example, at room temperature. A preferred reaction time is 30 minutes or more and 24 hours or less.

Prior to the staining with the fluorescent particle, a known blocking agent, such as BSA-containing PBS, is preferably added dropwise to the sample.

The stained tissue sample is then immersed in PBS in a vessel to remove unreacted fluorescent particle. The unreacted fluorescent particle may be removed at any temperature, for example, at room temperature. A preferred immersion time is 3 minutes or more and 30 minutes or less. PBS may be replaced with fresh one during the immersion when necessary. The tissue sample is covered with a cover glass to seal the tissue sample. A commercially available sealant may be used when necessary.

In the case where staining with an HE staining reagent is performed, HE staining is followed by the sealing of the tissue sample with the cover glass.

[Acquisition of Fluorescent Image]

A wide-field microscopic image (fluorescent image) of the stained tissue sample is taken with a microscopic imaging device 1A. In the microscopic imaging device 1A, an excitation light source and an optical filter for detecting fluorescent light are selected according to the absorption maximum wavelength of the fluorescent substance used in the staining reagent and the wavelength of the fluorescent light from the fluorescent substance.

Operation of Pathological Diagnosis Support System 100

The operation of the pathological diagnosis support system 100 for biological substance quantitation (including staining, image acquisition, and analysis described above) will now be described in reference to the flowchart in FIG. 5. Throughout the specification, the operation will be described in an exemplary case in which a target sample is a tissue sample stained with a staining reagent containing a fluorescent particle bonded to a biological substance recognition site that can recognize a specific protein (HER2 protein in breast cancer tissues in the present specification; hereinafter, referred to as a specific protein) and in which a standard sample is plural kinds of cells cultured on a substrate, such as a commercially available microscopic slide, but should not be limited to this case. Any sample is included as long as it can be bonded to the fluorescent particle bonded to biological substance recognition site, such as biotin or antigen in which concentration of the biological substance is known.

First, an operator quantitates concentration of the specific protein in the cultured cells, which is the standard sample of the present embodiment (step S1). The concentration of the specific protein can be quantitated by any known method, for example, ELISA, flow cytometry, Western blotting, and the like. The concentration of the specific protein per cell can be thereby calculated. According to ELISA and Western blotting, the concentration of the specific protein can be quantitated from cells dissolved in a predetermined solution. According to flow cytometry, biological molecules per cell can be detected and quantitated from cells scattered in a predetermined solution by light scattering or fluorescence measurement with laser beam.

As a standard sample, the operator selects cultured cells in the same lot and having the same quality as the cultured cells in which concentration of the specific protein is quantitated. Any number of kinds of standard samples may be selected. In order to obtain a highly accurate quantitation result by making calibration curves based on the measurement result from the standard samples, plural kinds of standard samples are preferably used. The plural kinds of standard samples preferably have widely different concentration of specific protein quantitated in step S1 are from each other.

Subsequently, the operator prepares formalin-fixed and paraffin-embedded slices of a target sample(s) and standard samples (step S2) and then stains the target sample and standard samples respectively under the same staining conditions with two different kinds of staining reagent (i.e. HE staining reagent and a staining reagent including the fluorescent particle as a fluorescent labelling material, which is bonded with a biological substance recognition site recognizing the specific protein) (step S3).

Staining under the same condition means that, for example, one operator performs staining process using staining reagents in the same lot, and that the time, temperature, and humidity in each staining step are substantially constant. It is preferred that one operator performs staining of the target sample and the standard samples sequentially and in parallel using the staining reagents in the same lot, so that the staining conditions can be easily constant.

After that, a fluorescent image and a bright field image of each sample (the target sample and the standard samples) are respectively obtained with the microscopic image acquiring device 1A according to the procedures (a1) to (a5). The images are input into the image processing device 2A and analyzed (step S4). The images of the target sample and the standard samples are obtained and analyzed under the same conditions.

(a1) The operator places each of the target sample and the standard samples stained with the HE staining reagent and the staining reagent containing the fluorescent particle on a microscopic slide, and sets the slide on the slide fixation stage of the microscopic image acquiring device 1A;

(a2) The operator sets a bright field unit, and adjusts the magnification for photographing and the focus so that the target region of the tissue is in the field;

(a3) The operator photographs the sample with the photographing unit to generate image data of the bright field image, and transmits the image data to the image processing device 2A;

(a4) The operator replaces the bright field unit with a fluorescence unit; and (a5) The operator photographs the sample with the photographing unit without changing the field and the magnification to generate image data of the fluorescent image, and transmits the image data to the image processing device 2A.

Figure 6:
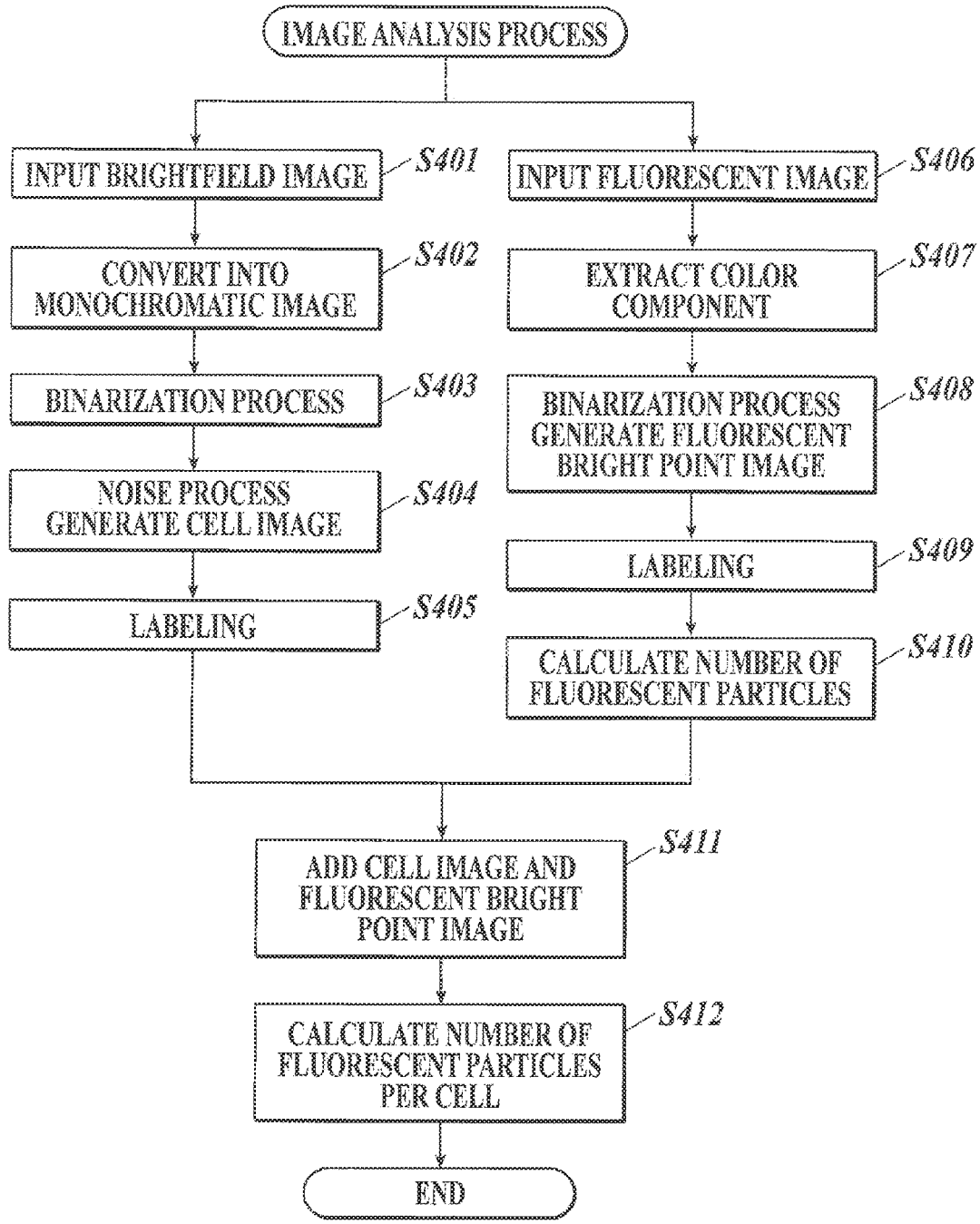
FIG. 6 is a flowchart illustrating detailed process in Step S4 of FIG. 5.

Obtaining and analyzing images of the target sample and the standard samples under the same conditions means that, specifically, the fluorescent image and the bright field image are respectively obtained with the same microscopic image acquiring device 1A under the same conditions (for example, exposure time, magnification, white balance, and the like), and the cell image and the fluorescent bright spot image are respectively extracted using the same threshold value and under the same noise processing condition in each step in FIG. 6.

In the image processing device 2A, image analysis is performed on the basis of the bright field image and the fluorescent image input from the microscopic image acquiring device 1A. An evaluation value is measured to show the quantitative evaluation of fluorescence from the fluorescent bright spots in a cell (step S4). In the present embodiment, a fluorescent particle is used as fluorescent labelling material and the number of the fluorescent particle is determined as the evaluation value, but the present invention should not be limited to this. For example, integrated value of the fluorescent luminance may be determined as the evaluation value.

FIG. 6 illustrates a detailed flowchart of the image analysis in step S4. The image analysis illustrated in FIG. 6 is executed in cooperation with the controller 21 and the program stored in the storage 25.

When the bright field image transmitted from the microscopic image acquiring device 1A is input into the communication interface 24 (Step S401), a cell region is extracted from the bright field image (Step S402 to step S405).

Figure 7A:
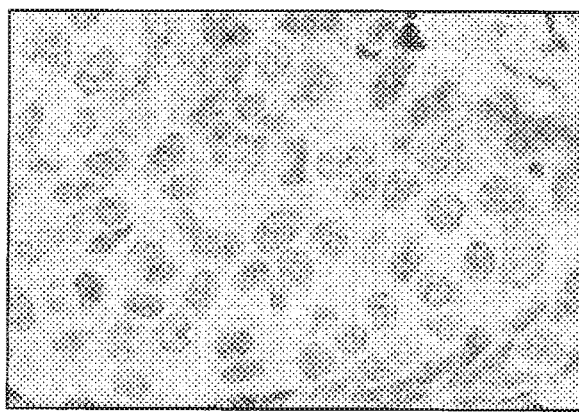
FIG. 7A is a diagram illustrating an exemplary bright field image.

In extracting a cell region, the bright field image is converted into a monochromatic image (Step S402). FIG. 7A illustrates an exemplary bright field image.

The monochromatic image is binarized using a predetermined threshold value (Step S403).

Figure 7B:
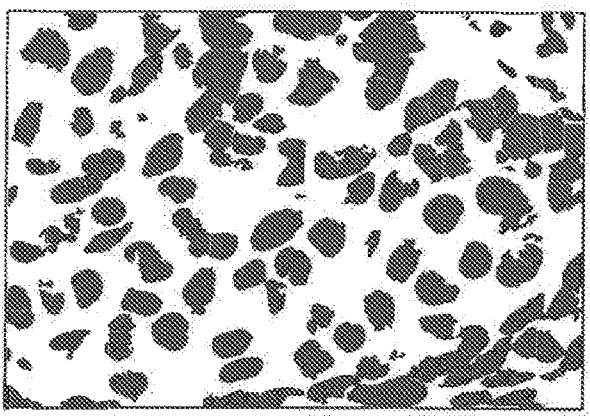
FIG. 7B is a diagram illustrating an image (cell image) of cell regions extracted from the bright field image in FIG. 7A.

In the next step, noise reduction process is performed (Step S404). The noise reduction can be performed, for example, by subjecting the binarized image to a closing process. The closing process includes dilation process followed by erosion process executed as many times as the dilation process. In the dilation process, a target pixel is replaced with a white pixel if at least one white pixel is present within the range of n×n pixels from the target pixel (where n is an integer of 2 or more). In the erosion, the target pixel is replaced with a black pixel if at least one black pixel is present within the range of n×n pixels from the target pixel. The closing process can remove small regions such as noise. FIG. 7B illustrates an exemplary image after the noise reduction process. An image of extracted cell regions (cell image) is obtained after the noise reduction process as in FIG. 7B.

In the next step, the image after the noise reduction process is subjected to labelling process to assign label to each of the extracted cells (Step S405). In the labelling process, the same label (number) is assigned to contiguous pixels in an image for identification of an object. By the labelling process, the cells in the image after noise reduction can be identified and labelled.

Meanwhile, when the fluorescent image transmitted from the microscopic image acquiring device 1A is input into the communication interface 24 (Step S406: fluorescent image input step or standard fluorescent image input step), bright spot regions representing the presence of the fluorescent particle are extracted from the fluorescent image, and the fluorescent particle number in the bright spot regions is calculated (Steps S407 to S410: fluorescence quantitation step or standard fluorescence quantitation step).

Figure 8A:
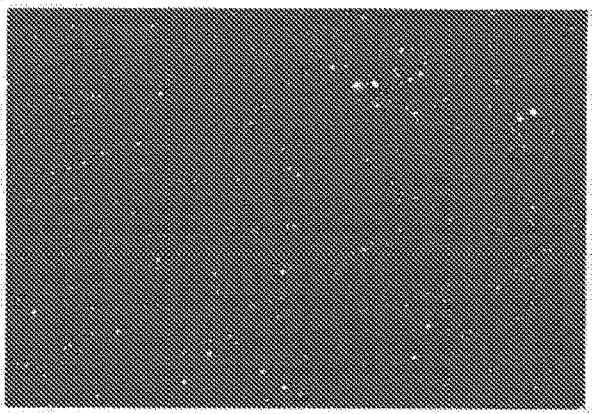
FIG. 8A is a diagram illustrating an exemplary fluorescent image.

At first, color components are extracted from the fluorescent image as in FIG. 8A, according to the emission wavelengths of the fluorescent bright spots (Step S407).

Figure 8B:
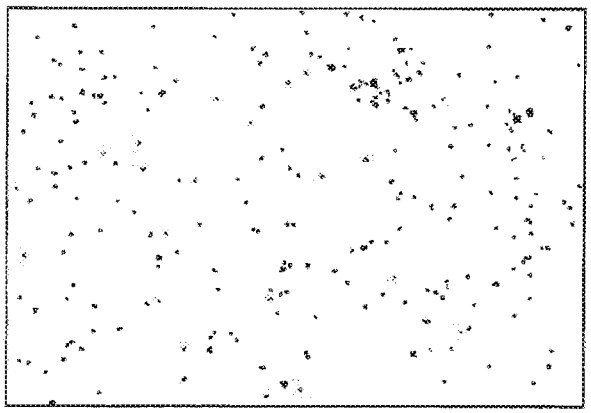
FIG. 8B is a diagram illustrating an image (bright point image) of bright spot regions extracted from the fluorescent image in FIG. 8A.

In Step S407, when the emission wavelength of the fluorescent particle is 615 nm, for example, only the fluorescent bright spots having the wavelength of 615 nm are extracted as an image. In the next step, the extracted image is subjected to a binarizing process using a predetermined threshold to generate a bright spot image of extracted bright spot regions (Step S408). FIG. 8B illustrates an exemplary bright spot image.

Noise removal process for removing autofluorescence of cells or other unnecessary signal components may be executed prior to the binarizing process. A low-pass filter, such as a Gaussian filter, or a high-pass filter, based on a second derivative, is preferably used.

Subsequently, labelling process is executed to label each of the extracted bright spot regions (Step S409).

Subsequently, the fluorescent particle number in each extracted bright point region is calculated (step S410). The fluorescent particle number may be calculated by any method, for example, on the basis of the integrated value of the luminance in each bright spot region.

After the process in step S410, the cell image (FIG. 7B) and the image of extracted bright spot regions (FIG. 8B) are added (step S411), the distribution of the bright spot regions in cells are shown at the display 23 of the image processing device 2A, and the fluorescent particle number per cell region is calculated (step S412).

Figure 5:
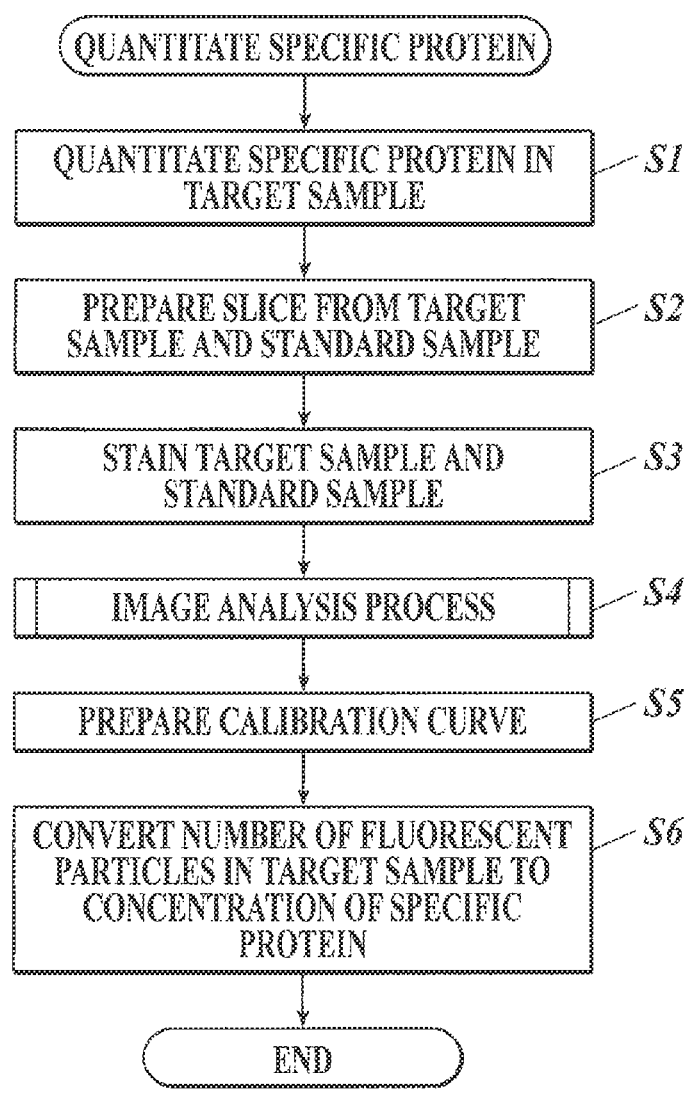
FIG. 5 is a flowchart illustrating steps for biological substance quantitation executed in the pathological diagnosis assistance system according to the present invention.

After the process in step S412, the process returns to the steps in FIG. 5 to prepare a distribution diagram and a calibration curve based on the distribution diagram (step S5: correlation calculation step). The distribution diagram shows a correlation between the concentration of the specific protein in each standard sample measured in step S1 and the fluorescent particle number per cell in the standard sample measured in step S4, respectively plotted on a horizontal axis and on a vertical axis.

Subsequently, the fluorescent particle number per cell in the target sample calculated in step S4 is converted to the concentration of specific protein on the basis of the calibration curve prepared in step S5 (step S6: conversion step).

According to the above-described present embodiment, the target sample which is an observation target and the standard samples in which concentration of the specific biological substance is quantitated in advance are prepared through the processes in Steps S1 to S2. Staining and image analysis under the same conditions are performed for the target sample and the standard samples through the processes in steps S3 to S4. The fluorescent particle number in the target sample is converted to the concentration of the specific protein through the processes in steps S5 to S6. Because the fluorescent particle number in the target sample is converted to the concentration of the specific protein on the basis of the measurement result for the standard sample measured under the same conditions, the quantitation result of the specific protein can be compared and evaluated even when at least one of the operator, constitution of the pathological diagnosis support system 100, and the measurement conditions is different.

The above-descried embodiment is a suitable example of the present invention, and the present invention should not be limited to this.

For example, in step S6, the specific protein may be quantitated without preparation of calibration curve. For example, the amount of the specific protein can be calculated on the assumption that the ratio of the fluorescent particle number to the amount of the specific protein per cell of the standard sample is equivalent to that of the target sample. Thus, the quantitation of the specific protein can be easily performed on the basis of only one of standard sample. However, considering the accuracy in quantitating the specific protein, it is preferred that the calibration curve is prepared on the basis of a plurality of standard samples.

It is generally known that the calibration curve for immunostaining shows a sigmoid shape, when it is prepared on the basis of the antigen concentration plotted on a horizontal logarithmic axis and the evaluation value of staining on a vertical axis. Accordingly, the calibration curve of the present invention prepared in step S6 in FIG. 5 is preferably a sigmoid curve approximated to the distribution of the antigen concentration and the evaluation value of fluorescence. More preferably, only the most inclined portion of the prepared sigmoid curve is linearly approximated and used as a calibration curve. The range for the linear approximation may be determined by any method. For example, a calibration curve may be determined as an approximate straight line only within the range of the specific protein concentration at which the correlation coefficient of the approximate straight line is more than a predetermined value.

A sample of cultured cell is preferably used as a standard sample in the present embodiment because many homogenous samples can be easily obtained so that there is strong correlation between the concentration of the specific protein and the fluorescent particle number using many samples. Accurate quantitation result can be thereby obtained.

In the present embodiment, the fluorescent substance used as a staining reagent is described as a fluorescent particle in which a plurality of molecules of the fluorescent substance are accumulated, but may be one molecule of fluorescent substance bonded to a biological substance recognition site.

However, the high fluorescence from a fluorescent particle is hardly affected by noise due to photographic environment, such as environment light in the room or the efficiency of the image acquiring device. Furthermore, by using the fluorescent particle, not only the fluorescent luminance but the fluorescent particle number can be measured and quantitated from the fluorescent image. Furthermore, the luminance of one particle is hardly affected by the time required for image acquisition (for example, exposure time of excitation light) or the storage condition of the stained samples, because the fluorescent particle hardly photobleaches. Accordingly, the fluorescent particle yields less error in the evaluation result of fluorescence when used as a staining reagent, compared to the fluorescent substance which does not compose a fluorescent particle. The highly accurate quantitation result of the biological substance is thereby obtained. Considering the above, the fluorescent particle is preferably used as the staining reagent in the present invention.

In step S5 of the present embodiment, the fluorescent particle number is measured per cell, however, it may be measured per cell nucleus or per image area of the observation target, for example.

In the present embodiment, only one kind of specific protein is quantitated, however, plural kinds of specific protein may be stained using two or more fluorescent substances having different emission wavelength from each other.

In such case, each of the color components is extracted using filters in Step S507, the processes in Steps S508 to S509 are executed for each of the extracted color components (wavelength components), and a cell image and fluorescent particle images for each of the color components are superimposed in Step S11.

The fluorescent particle may be bonded to the biological substance recognition site which bonds to a specific biological substance directly as in the above embodiment or indirectly through other materials as in the indirect method publically known in the field of immunostaining. For example, after the tissue sample is reacted with a primary antibody directed against the specific antibody, the tissue sample is further reacted with a secondary antibody directed against the primary antibody and bonded to a fluorescent particle so that the specific protein is stained. Otherwise, after the tissue sample is reacted with a primary antibody directed against the specific antibody and further with a biotinylated secondary antibody directed against the primary antibody, the tissue sample is reacted with a fluorescent particle modified with streptavidin. In this case, the specific protein is stained using the specific bond of the streptavidin and the biotin to form a complex.

The description above discloses an example in which an HDD or a semiconductor nonvolatile memory is used as a computer-readable medium for the program according to the present invention, but the present invention should not be limited to this. Another computer-readable medium may also be used, for example, a portable recording medium, such as CD-ROM. Carrier waves can also be used as a medium that provides data of the program according to the present invention through a communication line.

The detailed configurations and the operations of the devices forming the pathological diagnosis support system 100 can also be appropriately modified within the scope of the present invention.

The following VERIFICATION EXPERIMENTS 1 and 2 show the quantitation results by conventional method (comparative examples) and the quantitation results obtained by correcting the comparative examples with the method of the present invention (present invention). The staining conditions (concentration of the staining reagent) for staining Ki67 protein in the tissue samples and the image acquiring condition (exposure time of excitation light (fluorescence)) were intentionally changed in the experiments.

Verification Experiment 1

(A) Quantitation Using a Staining Reagent Including 0.02 NM of Fluorescent Particle
(A-0) Preparation of Staining Reagent
[Preparation of Fluorescent Substance-Encapsulating Melamine Nanoparticle]

Sulfo Rhodamine 101 (a red fluorescent dye made by Sigma-Aldrich Corporation) (14.4 mg) as a fluorescent substance was dissolved in water (22 mL). A 5% aqueous solution (2 mL) of an emulsifier for emulsion polymerization EMALGEN (registered trademark) 430 (polyoxyethylene oleyl ether, made by Kao Corporation) was added to the solution. The solution was heated to 70° C. with stirring on a hot stirrer, and 0.65 g of a melamine resin raw material NIKALAC MX-035 (made by NIPPON CARBIDE INDUSTRIES CO., INC.) was added to the solution.

A 10% aqueous solution (1000 μL) of dodecylbenzenesulfonic acid (made by KANTO CHEMICAL CO., INC.) as a surfactant was added to the solution, and was stirred at 70° C. for 50 minutes. The solution was heated to 90° C., and was stirred for 20 minutes at the temperature. The obtained dispersion of resin particle with dye was washed with pure water to remove impurities, such as excess resin raw material and excess fluorescent dye.

Specifically, the dispersion was centrifuged with a centrifuge (Micro Cooling Centrifuge 3740 made by Kubota Corporation) at 20000 G for 15 minutes and the supernatant was removed. Ultrapure water was added, and the solution was redispersed by ultrasonic waves. The centrifugation, removal of the supernatant, and redispersion in ultrapure water was repeated five times. The obtained melamine particle was positively charged, due to a lot of amino groups in the skeleton of the melamine resin. The evaluation of charge of the resin particle was performed by component analysis of resin by NMR, IR, and the like, and by measurement of zeta potential.

The obtained nanoparticle 1 was observed with a scanning electron microscope (SEM; S-800 made by Hitachi, Ltd.). The average particle size was 150 nm and the coefficient of variation was 12%.
[Bonding of Antibody to Fluorescent Particle]

An anti-Ki-67 antibody was bonded to the fluorescent particle by the following Steps (1) to (12).
Step (1): Disperse 1 mg of the fluorescent particle 1 in 5 mL of pure water. Next, add 100 μL of an aminopropyltriethoxysilane aqueous dispersion (LS-3150; Manufactured by Shinetsu Kagaku Co., Ltd.) thereto and perform stirring for 12 hours at room temperature.
Step (2): Perform centrifugation on the reacted mixture at 10,000 G for 60 minutes and remove the supernatant.
Step (3): Add ethanol and disperse the precipitates and perform centrifugation again. By the same procedure, perform washing with ethanol once and washing with pure water once.

The obtained fluorescent particle modified with the amino group was subjected to FT-IR measurement. Adsorption derived from the amino group was observed, and it was confirmed that the particle had been modified with the amino group.
Step (4): Adjust the fluorescent particle modified with the amino group obtained in Step (3) to 3 nM using PBS containing 2 mM of EDTA (ethylenediaminetetraacetic acid).
Step (5): Mix the adjusted solution in Step (4) with SM(PEG) 12 (Thermo Scientific, succinimidyl-[(N-maleomidopropionamid)-dodecaethyleneglycol]ester) so that the final concentration is 10 mM, and perform reaction for 1 hour.
Step (6): Perform centrifugation on the reacted mixture at 10,000 G for 60 minutes and remove the supernatant.
Step (7): Add PBS containing 2 mM of EDTA to disperse the precipitates and perform centrifugation again. With the same procedure, perform washing three times. Finally, perform re-dispersion by using 500 μL of PBS.
Step (8): Dissolve 100 μg of an anti Ki67 antibody in 100 μL of PBS, add 1M dithiothreitol (DTT) thereto, and make it react for 30 minutes.
Step (9): Remove excessive DTT from the reacted mixture with a gel filter column to obtain a reduced anti Ki67 antibody solution.
Step (10): Mix the particle dispersion obtained at Step (7) with the fluorescent particle 1 as the starting material with the reduced anti Ki67 antibody solution obtained at Step (9) in PBS, and make it react for 1 hour.
Step (11): Add 4 μL of 10 mM mercaptoethanol so as to end the reaction.
Step (12): Perform centrifugation on the reacted mixture at 10,000 G for 60 minutes, remove the supernatant, and then add PBS containing 2 mM of EDTA so as to disperse the precipitates and perform centrifugation again. With the same procedure, perform washing three times. Finally, perform re-dispersion by using 500 μL of PBS, thereby obtaining the fluorescent particle with anti Ki67 antibody bonded.
(A-1) Preparation of Target Sample and Standard Sample Three spots ((a), (b), and (b)) were selected in a breast cancer array. The breast cancer array was cut into slices and determined to be target samples after fixing, dehydrating, and embedding the slices.

The expression amount of Ki67 protein was measured with ELISA kit (Human HER2 (Total) kit, No. KHO0701 made by Invitrogen Corporation) from the commercially available five kinds of cultured cell lines (CRL1500, NDA-MB175, COLO201, Hela, and NDA-MB231). The cultured cell lines respectively in the same lot as the above five kinds of cultured cell lines were determined as standard samples.
(A-2) Staining of Tissue with Fluorescent Particle Immunostaining of target samples and standard samples was performed by the following Steps (1) to (11). The same operator performed the immunostaining of the target samples and standard samples in parallel, so that the immunostaining was performed almost at the same time and under the same conditions.
Step (1): Immerse the target sample or the standard sample in a container containing xylene for 30 minutes. Change the xylene three times during the immersion.

Step (2): Immerse the target sample or the standard sample in a container containing ethanol for 30 minutes. Change the ethanol three times during the immersion.
Step (3): Immerse the target sample or the standard sample in a container containing water for 30 minutes. Change the water three times during the immersion.
Step (4): Immerse the target sample or the standard sample in 10 mM citric acid buffer solution (pH 6.0) for 30 minutes.
Step (5): Perform autoclaving for 10 minutes at 121 degrees.
Step (6): Immerse the target sample or the standard sample in a container containing PBS for 30 minutes.
Step (7): Put 1% BSA-containing PBS on the target sample or the standard sample and leave it as it is for 1 hour.
Step (8): Put the staining reagent diluted with 1% BSA-containing PBS to 0.02 nM on the target sample or the standard sample and leave it as it is for 3 hours.
Step (9): Immerse the target sample or the standard sample in a container containing PBS for 30 minutes.
Step (10): Perform hematoxylin staining after fixation with 4% neutral Paraformaldehyde solution for 10 minutes.
Step (11): Drip Aquatex, produced by Merck Chemicals, thereon and then place a cover (A-3) Acquiring Microscopic Image With respect to each of the target samples and the standard samples, microscopic images (a bright field image and a fluorescence image) were acquired.

As a microscope, an upright microscope Axio Imager M2 (produced by Carl Zeiss AG) was used. The objective lens was set to 20 times. In obtaining a fluorescence image, each tissue section was irradiated with excitation light having a wavelength of 580 nm for exposure time of 200 mn, an image of fluorescence having a wavelength of 610 nm emitted from the tissue section was formed, and a microscopic image (image data) was acquired with a camera (monochrome) set in the microscope. The camera has 6.4 μm×6.4 μm as the pixel size, 1,040 pixels as the number of pixels in height and 1,388 pixels as the number of pixels in width (a capturing region of 8.9 mm×6.7 mm).

The fluorescent images of the target samples and the standard samples were obtained almost at the same time and under the same conditions by the same operator with the same apparatus.

(A-4) Calculation of Fluorescent Particle Number Per Cell

The microscopic images of the target samples and the standard samples obtained in (A-3) were subjected to image analysis illustrated in FIG. 6 and the fluorescent particle number per cell was calculated as an evaluation value of fluorescence. In calculating the fluorescent particle number, a binary image was prepared based on a predetermined higher threshold and a lower threshold. The fluorescent particle number was counted with bright spot measuring software "G-count" made by G-Angstrom K.K. After that, the bright field image obtained in (A-3) and the fluorescent image was superimposed. The number of bright spots in cell regions were calculated and thus the fluorescent particle numbers in a cell were calculated for the target samples and the standard samples, respectively. The fluorescent particle number in a cell of the target sample (fluorescent particle number/cell) is determined as COMPARATIVE EXAMPLE 1.

(A-5) Quantitation of Expression Amount of Ki67 Protein in One Cell

Figure 9:
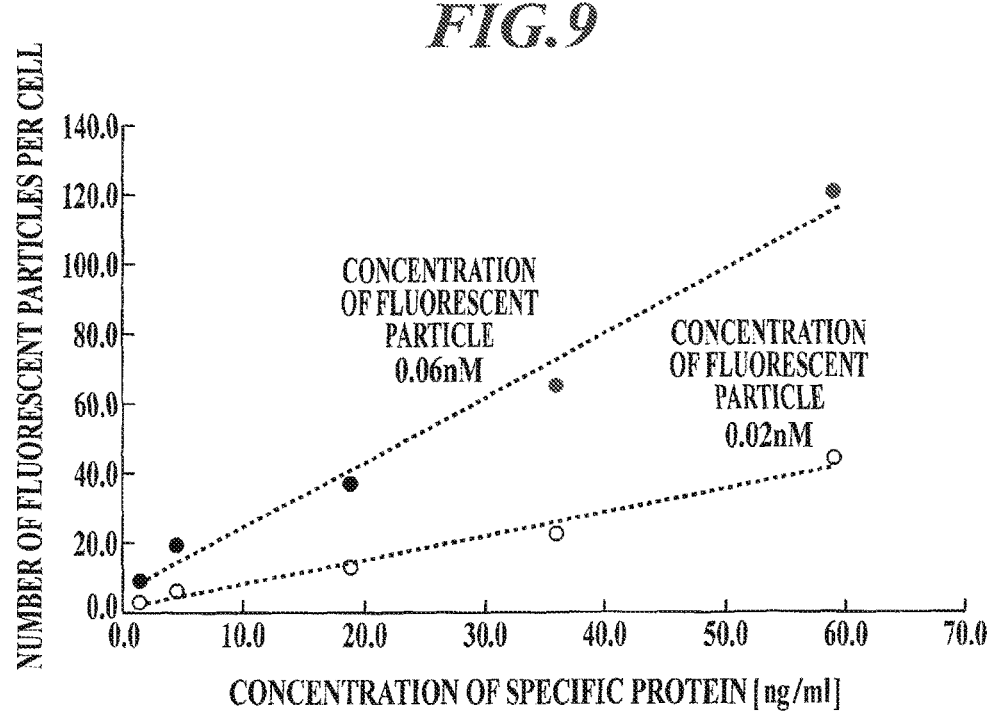
FIG. 9 is a diagram illustrating exemplary calibration curves using different concentrations of staining reagent.

As shown in FIG. 9, the distribution diagram was prepared. In the diagram, the horizontal axis represents the expression amount of Ki67 protein previously measured from the cultured cell line in the same lot as the standard sample. The vertical axis represents the fluorescent particle number in a cell of the standard sample calculated in (A-4). Dotted lines in FIG. 9 are calibration curves obtained by linear approximation of the distribution. The fluorescent particle number in a cell of the target samples was converted to the concentration (ng/ml) of Ki67 protein in a cell of the target samples on the basis of the calibration curves and was determined as PRESENT INVENTION 1.

(B) Quantitation Using a Staining Reagent Including 0.06 NM of Fluorescent Particle The fluorescent particle number per cell was quantitated in each of the target samples and the standard samples as in the same processes as the above-described (A), except that staining reagent after dilution contains 0.06 nM of the fluorescent particle in step (8) of the above-described (A-2). The fluorescent particle number in a cell (fluorescent particle number/cell) of the target sample was determined as COMPARATIVE EXAMPLE 2. The fluorescent particle number in a cell of the target sample converted to the concentration of Ki67 protein (ng/ml) in a cell of the target samples was determined as PRESENT INVENTION 2.

Among the slices of the three spots ((a) to (c)) of the breast cancer array described in above (A-1), those adjacent to the three slices stained and used for quantitating Ki67 protein concentration in (A) was used as the target samples.

(C) Comparison of Quantitation Result with Different Concentration of Staining Reagent FIG. 9 shows calibration curves prepared in the quantitation step described in above (A) and (B). Each calibration curve was made by linear approximation of the fluorescent particle number in the fluorescent image plotted against the Ki67 protein concentration quantitated by ELISA for the five standard samples. While the gradient of the calibration curve was about 0.69 when the fluorescent particle concentration was 0.02 nM, it was about 1.85 when the fluorescent particle concentration was 0.06 nM. That is, the gradients were about three times different.

TABLE-1 shows the quantitation results of PRESENT INVENTIONS 1 and 2 and COMPARATIVE EXAMPLES 1 to 2.

TABLE-1

| | CONCENTRATION OF FLUORESCENT PARTICLE [nM] | SPOT (a) | SPOT (b) | SPOT (c) |
|---|---|---|---|---|
| PRESENT INVENTION 1 | 0.02 | 5.1 | 10 | 40.7 |
| PRESENT INVENTION 2 | 0.06 | 6.6 | 11 | 43.5 |
| COMPARATIVE EXAMPLE 1 | 0.02 | 4.8 | 8.2 | 29.3 |
| COMPARATIVE EXAMPLE 2 | 0.06 | 18 | 26.2 | 86.3 |

When the concentration of the fluorescent particle in the staining reagent increased by about three times, the quantitation results increased by about 2.4 to 3.1 times in all the spots (a) to (c) according to COMPARATIVE EXAMPLES 1 and 2, in which the quantitation results were the fluorescent particle number in a cell quantitated by the conventional method and without correction using calibration curves.

Meanwhile, even when the concentration of the fluorescent particle in the staining reagent increased by about three times, the quantitation results were about 0.77 to 0.94 times according to PRESENT INVENTIONS 1 and 2, in which the fluorescent particle number was converted to the concentration of the protein using calibration curves of FIG. 9 by the method of the present invention. The difference in quantitation results caused by the different concentration of the staining reagent was reduced by correction on the basis of calibration curves by the method of the present invention.

Verification Experiment 2

(D) Quantitation with Exposure Time of 100 MS in Fluorescent Image Acquisition

From the samples prepared and stained in above (A-1) and (A-2), the fluorescent particle number per cell was quantitated in each of the target samples and the standard samples in the same processes as the above-described (A-3) to (A-5), except that exposure time of excitation light was 100 ms in the above (A-3). The fluorescent particle number in one cell (fluorescent particle number/cell) of the target sample was determined as COMPARATIVE EXAMPLE 3. The fluorescent particle number in a cell of the target samples converted to the concentration of Ki67 protein (ng/ml) in a cell of the target samples was determined as PRESENT INVENTION 3.

TABLE-2 shows the quantitation results of PRESENT INVENTIONS 1 and 3 and COMPARATIVE EXAMPLES 1 and 3.

TABLE-2

|  | EXPOSURE TIME [ms] | SPOT (a) | SPOT (b) | SPOT (c) |
|---|---|---|---|---|
| PRESENT INVENTION 1 | 100 | 5.1 | 10 | 40.7 |
| PRESENT INVENTION 3 | 200 | 6 | 9.3 | 38.4 |
| COMPARATIVE EXAMPLE 1 | 100 | 4.8 | 8.2 | 29.3 |
| COMPARATIVE EXAMPLE 3 | 200 | 2.4 | 3.6 | 14.2 |

When the exposure time in fluorescent image acquisition was about 0.5 times, the quantitation results was about 0.5 to 0.57 times in any of the spots (a) to (c) according to COMPARATIVE EXAMPLES 1 and 3, in which the quantitation result was the fluorescent particle number in a cell quantitated by the conventional method and without correction using calibration curves.

Meanwhile, even when the exposure time in fluorescent image acquisition was about 0.5 times, the quantitation results were about 0.85 to 1.08 times according to PRESENT INVENTIONS 1 and 2, in which the fluorescent particle number was converted to the concentration of the protein by the method of the present invention as in the VERIFICATION EXPERIMENT 1. The difference in quantitation results caused by the different exposure time in fluorescent image acquisition was reduced by correction on the basis of calibration curves by the method of the present invention. Although embodiments of the present invention have been described and illustrated in detail, it is clearly understood that the same is by way of illustration and example only and not limitation, and the scope of the present invention should be interpreted by terms of the appended claims.

INDUSTRIAL APPLICABILITY

A specific biological substance in a tissue sample can be accurately quantitated by the present invention. The present invention can be particularly preferably applied in generating highly accurate information for pathological diagnosis.

DESCRIPTION OF REFERENCE NUMERALS 1A microscopic image acquiring device
2A image processing device
3A cable
21 controller (fluorescence quantitating unit, a standard fluorescent quantitation unit, a correlation calculation unit, a conversion unit)
22 operation unit
23 display
24 communication interface (fluorescent image inputting unit, standard fluorescent image inputting unit)
25 storage
26 bus
100 pathological diagnosis supporting system

The invention claimed is:

1. A method for quantitating an amount of a target substance in a sample stained with a staining reagent which stains the target substance with a fluorescent substance, the method comprising:
  inputting a fluorescent image which represents a presence of the target substance in the sample by a fluorescent bright spot;
  performing fluorescence quantitation which includes calculation of an evaluation value by quantitative evaluation of the fluorescent bright spot in the fluorescent image;
  inputting a standard fluorescent image under a same condition as the inputting of the fluorescent image, wherein
    the standard fluorescent image represents a presence of the target substance in a standard sample by a fluorescent bright spot based on staining under a same condition as the sample, and
    an amount of the target substance in the standard sample is measured in advance;
  performing standard fluorescence quantitation which includes calculation of an evaluation value by quantitative evaluation of the fluorescent bright spot in the standard fluorescent image under a same condition as the quantitation of fluorescence;
  calculating a correlation between the amount of the target substance in the standard sample and the evaluation value of the fluorescent bright spot in the standard fluorescent image; and
  converting the evaluation value of the fluorescent bright spot in the fluorescent image to an amount of the target substance in the sample based on the calculating of the correlation.

2. The method according to claim 1, wherein
  a calibration curve is prepared in calculating the correlation, wherein the calibration curve represents the evaluation value of the fluorescent bright spot of the standard fluorescence image corresponding to the amount of the target substance in the standard sample, and
  in the converting, the evaluation value of the fluorescent bright spot of the fluorescent image is converted to the amount of the target substance in the sample based on the calibration curve.

3. The method according to claim 1, wherein the standard sample is a cell cultured on a substrate.

4. The method according to claim 1, wherein the staining reagent comprises a fluorescent particle in which a plurality of molecules of the fluorescent substance are accumulated.

5. The method according to claim 4, wherein the florescent substance emits a light having a wavelength in the range of 400 to 1100 nm when excited by a light having a wavelength in the range of 200 to 700 nm.

6. The method according to claim 5, wherein the staining reagent comprises a plurality of the florescent particle, and the plurality of the florescent particle have an average particle diameter in a range of 40 to 280 nm.

7. The method according to claim 1, wherein the amount of the target substance in the standard sample is measured in advance by one of ELISA, flow cytometry, and Western blotting.

8. A pathological diagnosis support system which quantitates an amount of a target substance in a sample stained with a staining reagent which stains the target substance with a fluorescent substance, the system comprising:
   a storage which stores a program for quantitating the amount of the target substance; and
   a processor, the program causing the processor to function as:
   a fluorescent image inputting unit which inputs a fluorescent image which represents a presence of the target substance in the sample by a fluorescent bright spot;
   a fluorescence quantitation unit which calculates an evaluation value by quantitative evaluation of the fluorescent bright spot in the fluorescent image;
   a standard fluorescent image inputting unit which inputs a standard fluorescent image under a same condition as the fluorescent image inputting unit, wherein
      the standard fluorescent image represents a presence of the target substance in a standard sample by a fluorescent bright spot based on staining under a same condition as the sample, and
      an amount of the target substance in the standard sample is measured in advance;
   a standard fluorescent quantitation unit which calculates an evaluation value by quantitative evaluation of the fluorescent bright spot in the standard fluorescent image under a same condition as the fluorescence quantitation unit;
   a correlation calculator which calculates a correlation between the amount of the target substance in the standard sample and the evaluation value of the fluorescent bright spot in the standard fluorescent image; and
   a converter which converts the evaluation value of the fluorescent bright spot in the fluorescent image to an amount of the target substance in the sample based on the correlation.

9. A non-transitory recording medium storing a computer readable program causing a computer which quantitates an amount of a target substance in a sample stained with a staining reagent which stains the target substance with fluorescent substances, to function as:
   a fluorescent image inputting processor which inputs a fluorescent image which represents a presence of the target substance in the sample by a fluorescent bright spot;
   a fluorescence quantitation unit which calculates an evaluation value by quantitative evaluation of the fluorescent bright spot in the fluorescent image;
   a standard fluorescent image inputting unit which inputs a standard fluorescent image under a same condition as in the fluorescent image inputting unit, wherein
      the standard fluorescent image represents a presence of the target substance in a standard sample by a fluorescent bright spot based on staining under a same condition as the sample, and
      an amount of the target substance in the standard sample is measured in advance;
   a standard fluorescent quantitation unit which calculates an evaluation value by quantitative evaluation of the fluorescent bright spot in the standard fluorescent image under a same condition as the fluorescence quantitation unit;
   a correlation calculator which calculates a correlation between the amount of the target substance in the standard sample and the evaluation value of the fluorescent bright spot in the standard fluorescent image; and
   a converter which converts the evaluation value of the fluorescent bright spot in the fluorescent image to an amount of the target substance in the sample based on the correlation.

* * * * *